United States Patent
Zeller et al.

(10) Patent No.: US 11,054,494 B2
(45) Date of Patent: Jul. 6, 2021

(54) RECORDATION OF A MAGNETIC RESONANCE DATA SET

(71) Applicant: Siemens Healthcare GmbH, Erlangen (DE)

(72) Inventors: Mario Zeller, Erlangen (DE); Flavio Carinci, Wuerenlingen (CH); Dominik Paul, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/513,843

(22) Filed: Jul. 17, 2019

(65) Prior Publication Data
US 2020/0025850 A1    Jan. 23, 2020

(30) Foreign Application Priority Data
Jul. 17, 2018  (EP) .................................. 18183851

(51) Int. Cl.
*G01V 3/00* (2006.01)
*G01R 33/56* (2006.01)
(Continued)

(52) U.S. Cl.
CPC .......... *G01R 33/5608* (2013.01); *A61B 5/055* (2013.01); *G01R 33/286* (2013.01);
(Continued)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS 6,002,480 A * 12/1999 Izatt ...................... G01J 3/4412
356/479
8,089,278 B1 * 1/2012 Du ..................... G01R 33/4824
324/307
(Continued)

FOREIGN PATENT DOCUMENTS

DE    102016217863 A1    3/2018

OTHER PUBLICATIONS

Yun S.D. et al.: "Accelerated multiplexed-EPI with PSF-based distortion correction at 9.4T", Proceedings of the International Society for Magnetic Resonance in Medicine, Joint Annual Meeting ISMRM-ESMRMB, Nr. 1410, Apr. 28, 2014 (Apr. 28, 2014), p. 1410, XP040662479.
(Continued)

*Primary Examiner* — Walter L Lindsay, Jr.
*Assistant Examiner* — Frederick Wenderoth
(74) *Attorney, Agent, or Firm* — Schiff Hardin LLP

(57) ABSTRACT

Techniques are disclosed related to recording a magnetic resonance image data set of a region of a patient with a magnetic resonance device using a multislice imaging technique. The multislice technique may be applied simultaneously with at least partial undersampling in a slice plane. The magnetic resonance data may be read out from a set of excited slices simultaneously and, by means of a slice separation algorithm that is calibrated using reference data recorded in a separate reference scan, may be allocated to the simultaneously read-out slices. Subsequently, an undersampling algorithm compensating for the undersampling in the slice plane may be applied to the undersampled magnetic resonance data of the individual slices.

20 Claims, 4 Drawing Sheets

(51) Int. Cl.
 *A61B 5/055* (2006.01)
 *G01R 33/28* (2006.01)
 *G06T 5/50* (2006.01)
 *A61B 5/00* (2006.01)
 *G01R 33/48* (2006.01)
 *G01R 33/483* (2006.01)
 *G06T 11/00* (2006.01)

(52) U.S. Cl.
 CPC .............. *G06T 5/50* (2013.01); *A61B 5/0035* (2013.01); *G01R 33/4812* (2013.01); *G01R 33/4835* (2013.01); *G06T 11/003* (2013.01); *G06T 2207/10088* (2013.01)

(58) Field of Classification Search
 USPC ......................................................... 324/309
 See application file for complete search history.

(56) References Cited

U.S. PATENT DOCUMENTS

| | | | |
|---|---|---|---|
| 2014/0015527 A1* | 1/2014 | Griswold | G01R 33/4826 324/309 |
| 2014/0218026 A1* | 8/2014 | Moeller | G01R 33/561 324/309 |
| 2014/0376794 A1* | 12/2014 | Dumoulin | G01R 33/5611 382/131 |
| 2015/0323634 A1* | 11/2015 | Polimeni | G01R 33/56509 324/309 |
| 2015/0369893 A1* | 12/2015 | Takeshima | G01R 33/56545 324/309 |
| 2018/0081015 A1 | 3/2018 | Gebhardt et al. | |

OTHER PUBLICATIONS

Barth, Markus et al. "Simultaneous Multislice (SMS) Imaging Techniques", Magnetic Resonance in Medicine, vol. 75, pp. 63-81, 2016 // DOI: 10.1002/mrm.25897.

Setsompop, Kawin et al. "Blipped-Controlled Aliasing in Parallel Imaging for Simultaneous Multislice Echo Planar Imaging With Reduced g-Factor Penalty" Magnetic Resonance in Medicine; vol. 67; No. 5; pp. 1210-1224; DOI 10.1002/mrm.23097.; 2012.

European Search Report dated Jan. 25, 2019, Application No. 18183851.7.

* cited by examiner

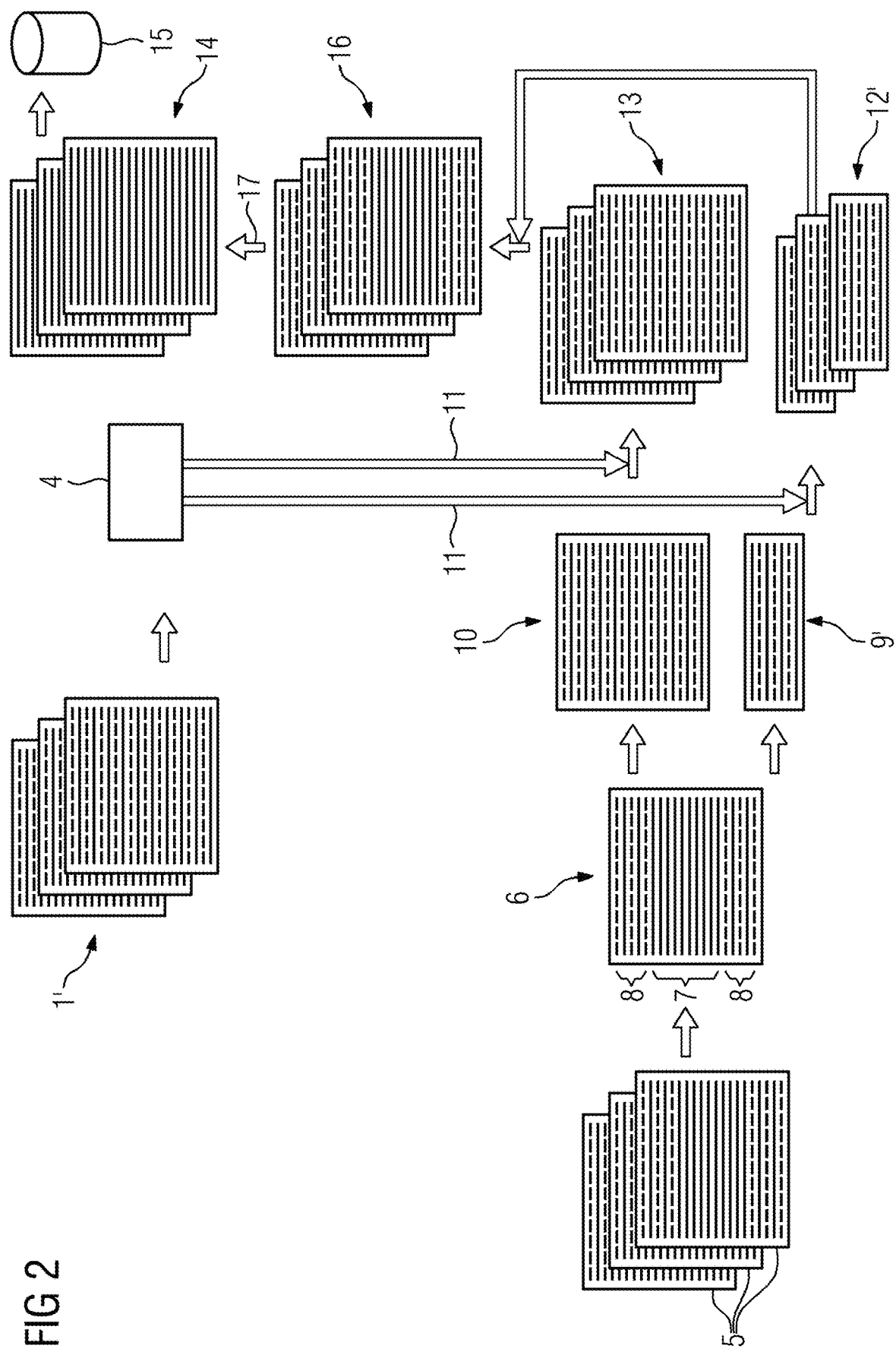

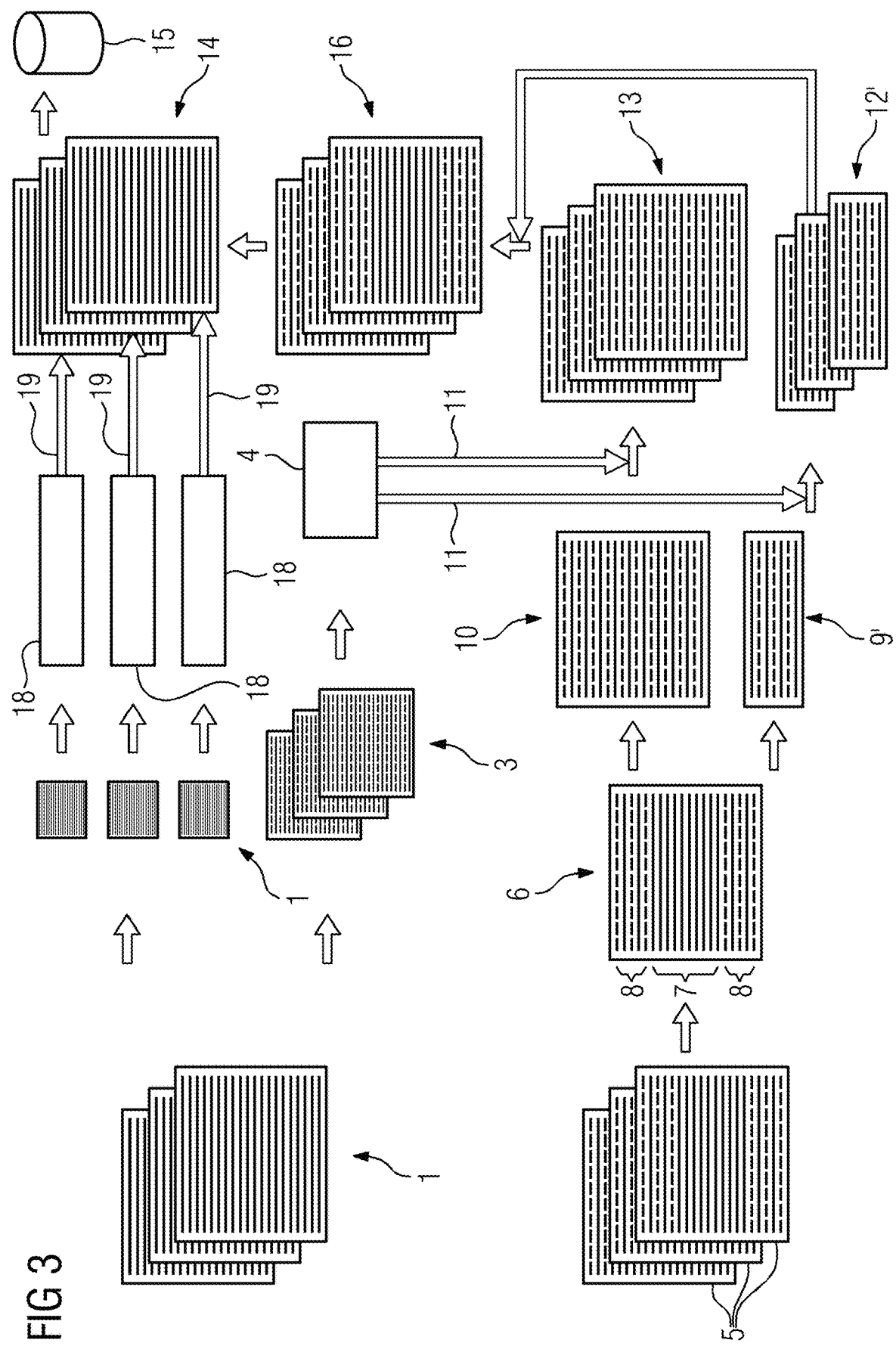

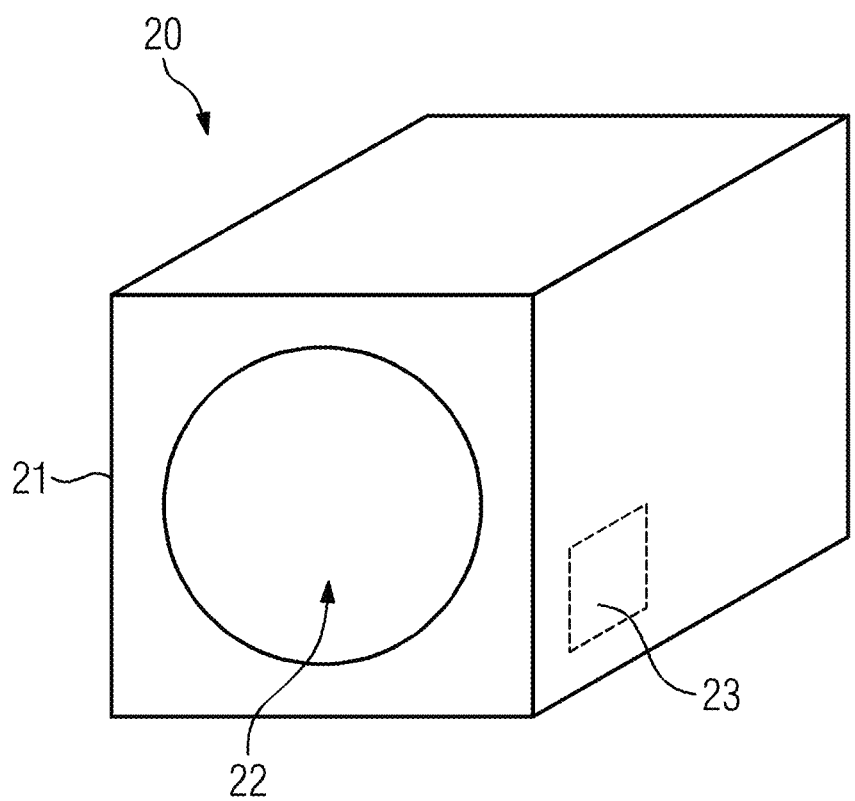

RECORDATION OF A MAGNETIC RESONANCE DATA SET

CROSS-REFERENCE TO RELATED APPLICATIONS

The present application claims the benefit of the filing date of European patent application no. EP 18183851.7, filed on Jul. 17, 2018, the contents of which are incorporated herein by reference in their entirety.

TECHNICAL FIELD

The present disclosure relates to a method for recording a magnetic resonance image data set of an investigation region of a patient with a magnetic resonance device using a multislice imaging technique.

BACKGROUND

Magnetic resonance imaging is a well-established modality for the recording of medical imaging data in examination regions of a patient. Since the duration of magnetic resonance examinations represents one of the most substantial problems of magnetic resonance imaging, a number of accelerated imaging techniques have been researched. Despite these efforts, current accelerated magnetic resonance imaging techniques still have various drawbacks.

SUMMARY

As noted above, current accelerated magnetic resonance imaging techniques have several issues. For example, one technique for accelerated magnetic resonance imaging includes first undersampling in the slice plane itself, with the missing k-space data being calculated by corresponding undersampling algorithms. These may include, for example, algorithms executed according to the in-plane Generalized Autocalibrating Partially Parallel Acquisitions (GRAPPA) method. Another approach to accelerated imaging is Simultaneous Multislice (SMS) imaging. For SMS imaging, by means of a common excitation module, a plurality of slices are excited within a repetition and the magnetic resonance signals from these slices are scanned simultaneously. Subsequently, magnetic resonance data is allocated by means of a slice separation algorithm (e.g., a slice GRAPPA algorithm), to the individual simultaneously recorded slices. Known simultaneous multislice imaging techniques include, for example, Hadamard encoding, methods with simultaneous echo refocusing, methods with broadband data uptake, or methods that use parallel imaging in the slice direction.

Furthermore, a another multislice imaging technique is referred to as "blipped CAIPI" (Controlled Aliasing In Parallel Imaging), and is a technique that was described by Setsompop et al. in "Blipped-Controlled Aliasing in Parallel Imaging for Simultaneous Multislice Echo Planar Imaging With Reduced g-Factor Penalty," Magnetic Resonance in Medicine 67, 2012, pages 1210-1224. As discussed in this article, to excite a plurality of slices simultaneously, a "multiband pulse" is used in which the pulse forms for all the bands are added together so that a baseband-modulated multiband pulse is formed. For each excited slice, a linear phase ramp in k-space is added in the slice direction. This linear phase generates a slice displacement in the image space. Furthermore, to reduce the "g-factor penalty," image displacements are induced between the slices during the readout module in that either gradient blips are output in the slice direction or the phase of the high frequency pulses is modulated. After the recording, the magnetic resonance data of the simultaneously excited slices is collapsed as a single slice. The magnetic resonance data can be separated during the post-processing by means of a slice separation algorithm, as described in the article. If an acceleration is also used in the slice plane (e.g., an undersampling), then the in-plane unaliasing takes place thereafter using an undersampling algorithm. In particular, an in-plane GRAPPA algorithm is used in a second step. As the result of the reconstruction, a magnetic resonance image data set is obtained.

Still further, the turbospin echo (TSE) sequence is one of the most often used magnetic resonance sequences in magnetic resonance imaging and can be used for a plurality of examination regions of the patient. The TSE sequence consists of a plurality of echo trains whereby, in each echo train, a plurality of k-space lines are recorded in the phase encoding direction after a single excitation pulse. This is achieved in that the spins are refocused by means of refocusing pulses after the recording of each k-space line. Compared to the conventional spin echo sequence, the recording time is accelerated by the number of refocused echoes in an echo train, i.e., the "turbo factor."

The TSE sequence (and other magnetic resonance sequences) can also be used for SMS imaging. To calibrate the slice separation algorithm and therefore to "deconvolute" the collapsed multiband data, reference data of a single-band reference scan is needed in which each slice, which is to be covered later by SMS imaging, is recorded individually. Known procedures in SMS-TSE imaging use a TSE or gradient echo reference scan that precedes the SMS data recording. It has been proposed in this regard to use the reference data both for calibrating the slice separation algorithm and for calibrating the undersampling algorithm.

Conventional TSE sequences that use an undersampling in the slice plane but do not use an SMS imaging technique support the complete sampling of a subregion of the scanned k-space around k-space center during the recording. The magnetic resonance data of this central subregion is used to calibrate the undersampling algorithms, and therefore to determine its kernels. The resonance data of this central subregion is also used to enable corresponding magnetic resonance data directly for the final magnetic resonance image data set, in that either an averaging is carried out for the central subregion or the (interpolated) k-space lines of the central subregion are entirely replaced by the recorded magnetic resonance data. This is beneficial to the signal-to-noise ratio (SNR) and reduces the SNR disadvantages that are inherent in the undersampling in the slice plane.

However, for SMS imaging techniques, this calibration method cannot be used since the calibration of the slice separation algorithm, in particular the slice GRAPPA algorithm, is possible only on regularly undersampled k-spaces to which the slice separation algorithm is then to be applied. Thus, for SMS imaging techniques, a reduced signal-to-noise ratio may result. To reduce this SNR loss, it has been proposed to adapt recording parameters such as, e.g., matrix size, phase oversampling, or the number of averagings. But doing so is extremely costly as the optimization is strongly dependent on the magnetic resonance protocol used, and a direct comparison between the magnetic resonance protocols that use SMS imaging and magnetic resonance protocols, which do not use SMS imaging, is more difficult.

Therefore, embodiments of the disclosure as described provide a possibility for improving the signal-to-noise ratio with simultaneous multislice imaging combined with undersampling in the slice plane.

As further discussed herein, the embodiments achieve this via a method, a magnetic resonance device, a computer program, and an electronically readable non-transitory medium.

In an embodiment, the method may include the magnetic resonance data being recorded, in at least two subregions of the sampled k-space in the slice plane with a different degree of sampling and before the use of the slice separation algorithm, such that the magnetic resonance data is divided into at least two portions, each associated with one subregion, each of a fixed degree of sampling, to which the slice separation algorithm is applied separately, whereby the portions are recombined slice by slice to determine the magnetic resonance image data set.

In an embodiment, it is proposed to also use SMS imaging, further to acquire additional k-space lines in the actual imaging scan, which are also used in the eventually reconstructed magnetic resonance data set for improving the signal-to-noise ratio. This means that a completely sampled subregion, (e.g., around k-space center), and an undersampled subregion of k-space (e.g., an outer region of the sampled k-space) are available. Nevertheless, to enable a slice separation by means of the slice separation algorithm (presupposing an even degree of sampling), the embodiments include subdividing the magnetic resonance data such that two portions having an even sampling level are formed. This means that the magnetic resonance data that are present with at least two different degrees of sampling are divided into at least two portions, each having their own constant degree of sampling for the portion.

In accordance with the embodiments as described herein, a slice separation algorithm is then applied to each of these portions (e.g., a slice GRAPPA algorithm), wherein different slice separation kernels, as described below in greater detail, can be used. In other words, the embodiments described herein permit the simultaneous multislice (SMS) imaging technology to be combined with recordings in which k-space center is completely sampled, whereby all the recorded magnetic resonance data is used to obtain an improved signal-to-noise ratio (SNR). This is achieved in that the recorded "collapsed" magnetic resonance data is suitably distributed in k-space and a separate slice separation is carried out for each portion. In this way, an improved signal-to-noise ratio is achieved.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 2 illustrates a second flow according to an exemplary embodiment;

FIG. 3 illustrates a third flow according to an exemplary embodiment; and

FIG. 4 illustrates a representation of a magnetic resonance device according to an exemplary embodiment.

The exemplary embodiments of the present disclosure will be described with reference to the accompanying drawings. The drawing in which an element first appears is typically indicated by the leftmost digit(s) in the corresponding reference number.

DETAILED DESCRIPTION

Figure 1:
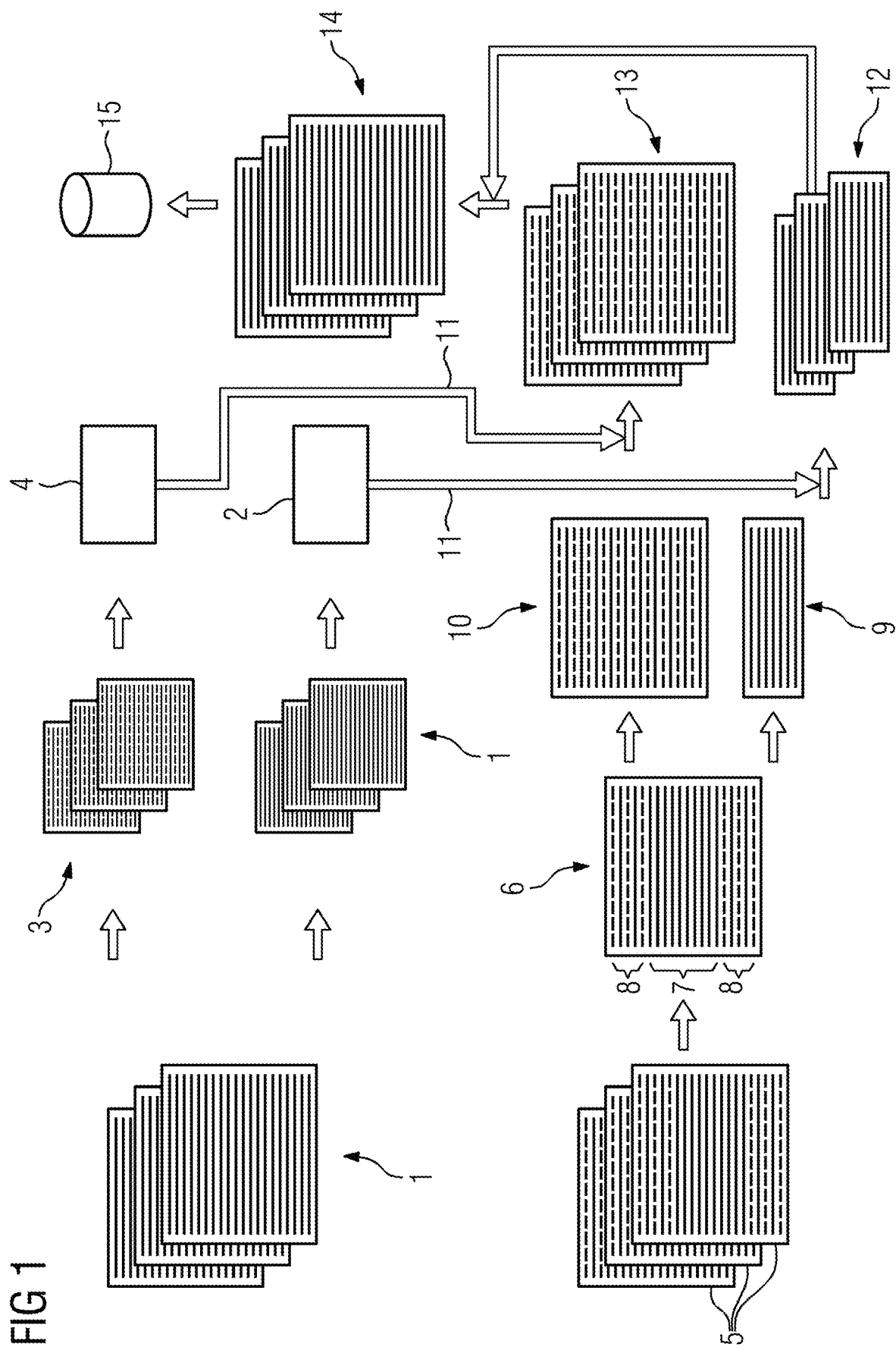
FIG. 1 illustrates a first flow according to an exemplary embodiment.

In an embodiment, any suitable type of slice separation algorithm (e.g., a slice GRAPPA algorithm), and/or any suitable type of undersampling algorithm (e.g., an in-plane GRAPPA algorithm) may be implemented. Advantageously, the magnetic resonance data may be recorded using a blipped CAIPI technique as the multislice imaging technique. Herein, the procedure described in the aforementioned article by Setsompop et al. can be utilized in its entirety. As a magnetic resonance sequence for the recording of the magnetic resonance data, a turbospin echo (TSE) sequence may be used, whereby the procedure can naturally also be applied to other magnetic resonance sequences, such as further spin echo-based or gradient echo-based sequence types, for instance.

In accordance with an embodiment, the reference data may be recorded with complete sampling of k-space and, by leaving out a part of the reference data, at least one slice separation kernel for the slice separation algorithm is determined. As a result, the artificial undersampling of the reference data corresponds to the undersampling of the portion for which the slice separation kernel is to be used. This means that it is entirely conceivable for the (separately to be performed) reference scan to carry out a high degree of sampling of k-space (e.g., a complete sampling), since to determine corresponding slice separation kernels to be applied to undersampled portions, an artificial undersampling can be achieved by omitting reference data for the creation of the corresponding degree of sampling. Such an embodiment is particularly useful, for example, if the reference data is also to be used for calibrating the undersampling algorithm, which is considered in closer detail below, but also if a plurality of slice separation kernels are to be determined for respective different degrees of sampling, for example for a complete sampling and for an undersampling, according to a particular degree of sampling.

Accordingly, an embodiment of the present disclosure provides that with at least two portions, each corresponding to a different degree of sampling, at least one corresponding slice separation kernel is determined in each case. In this way, highly sampled subregions of k-space, thus completely sampled subregions of k-space, can be further processed together, which leads to an improvement of the signal-to-noise ratio.

Thus, in an embodiment of the present disclosure which relates to a first, completely sampled subregion of k-space (e.g., around the k-space center), and to a second undersampled subregion of k-space, it can be provided that a slice separation kernel for both the degrees of sampling is determined from the reference data. In addition, the distribution of the magnetic resonance data takes place such that a first portion that corresponds to a degree of sampling of complete sampling comprises all the magnetic resonance data of the first subregion, whereas for the second portion, the magnetic resonance data of the second subregion is supplemented from magnetic resonance data of the first subregion such that a consistently similar degree of sampling is established.

Moreover, the respective slice separation kernels corresponding to the degree of sampling are applied by means of the slice separation algorithm to this first portion and the second portion. In this embodiment of the present disclosure, it is thereby advantageous if the separated magnetic resonance data of the completely sampled first subregion is also used for calibrating the undersampling algorithm (e.g., the in-plane GRAPPA algorithm). For the undersampled slice-separated magnetic resonance data, the undersampling algorithm is then applied, whereupon the magnetic resonance data of both portions is recombined again, either by replacing supplemented undersampled magnetic resonance data in the first subregion with the completely sampled magnetic resonance data or by averaging both the magnetic resonance data sets. By means of Fourier transforms of the recombined magnetic resonance data, the magnetic resonance image data set is then obtained. Thus, in this embodiment, an improvement in the signal-to-noise ratio has been achieved.

In an embodiment of the present disclosure, it can be provided that the distribution into portions takes place such that all the portions have the same degree of sampling. It is thereby achieved that all the portions have a degree of sampling corresponding to an undersampling, so that it is possible to record the reference data with the degree of sampling of the portions (i.e., undersampled). In addition, only one slice separation kernel of the slice separation algorithm needs to be calculated. Overall, this advantageously enables the external reference data set being recorded undersampled, so that scanning time can be saved and reduced calculation effort (e.g., processing resources) is required, since only a single slice separation kernel needs to be calculated.

An embodiment of the present disclosure facilitates that, upon complete sampling of a first subregion (e.g., about k-space center) and undersampling of a second subregion comprising the remaining k-space, from the first subregion k-space lines are added to a second portion comprising magnetic resonance data of the second subregion with imagined continuation of the sampling pattern of the second subregion, and the remaining magnetic resonance data of the first subregion in at least one first portion, the undersampling of which corresponds to that of the first portion, is further processed. For example, during an undersampling in the slice plane by the factor 2 as the degree of sampling of the second subregion, every second line of the first subregion may be assigned to the second portion, and the remaining k-space lines of the first subregion may be used as a first portion.

In other words, the completely sampled (e.g., central) first subregion may be divided into two or more portions so that the completely sampled magnetic resonance data is therefore divided between at least two portions. The number of portions is thereby determined by means of the in-plane acceleration factor (with the factor 2, as stated above), a single first portion and a second portion (with the factor 3), two second portions and one second portion, etc. Thereby, the sampling pattern of the second subregion (and therefore of the degree of sampling), is maintained for all portions, so that none of the portions comprises a completely sampled region of the k-space, and all the portions can be slice-separated using the same slice-separation kernel in the slice separation algorithm. After this slice separation, all the slice-separated portions are recombined again, whereby the completely sampled, in particular, central first subregion can be used for the calibration of the undersampling algorithm. By means of the undersampling algorithm, the missing k-space lines in the second subregion are then supplemented and the magnetic resonance data set can be obtained by using a Fourier transform.

It should be mentioned that it is not unavoidably necessary to carry out the calibration of the undersampling algorithm from completely sampled magnetic resonance data of the actual imaging scan. This means that exemplary embodiments are also conceivable in which at least one completely sampled part of the reference data is used for calibrating the undersampling algorithm. However, as compared with a complete undersampling, additional k-space lines are sampled during the recording of the magnetic resonance data, and can be used for improving the signal-to-noise ratio of the resulting magnetic resonance image data set, in that they are also slice-separated and are fed to the determination of the magnetic resonance image data set again as described above.

Moreover, with many magnetic resonance sequences for recording the magnetic resonance data, there are already time windows in which these additional k-space lines can be sampled without a substantial loss of time, so that a magnetic resonance data set having a different degree of sampling comes about and can be processed as described here. This means, however, an improvement in the signal-to-noise ratio can be achieved according to the present embodiments as described herein if a relatively small first subregion that would not suffice for calibrating the undersampling algorithm is completely sampled.

With regard to the signal-to-noise ratio, if may be particularly useful to use magnetic resonance data of a subregion of a higher (complete) degree of sampling at least partially for calibrating the undersampling algorithm, and therefore with regard to the undersampling algorithm, at least partially to allow a calibration integrated into the actual imaging scan.

In an embodiment, both magnetic resonance data of a completely sampled subregion as well as at least one completely sampled part of the reference data may be used for calibrating the undersampling algorithm. In doing so, reference data for the undersampling algorithm can result both from the external reference scan and also from completely sampled subregions of the imaging scan, so that a further improvement of the stability and the robustness is achieved as compared with a movement in relation to the calibration of the undersampling algorithm.

As further discussed herein, embodiments of the present disclosure also relate to a magnetic resonance device comprising a control device for performing the method according to the embodiments described herein. The embodiments relating to the method according to the disclosure can be executed via the magnetic resonance device with which the aforementioned advantages can therefore also be achieved. For this purpose, the control device can comprise, for example, at least one processor and/or at least one storage means (e.g., a non-transitory computer-readable medium) can have, for example, a sequence unit configured to receive the reference data and the magnetic resonance data as well as a calibration unit for configured to calibrate the slice separation algorithm and the undersampling algorithm. Furthermore, the control device can comprise a distributing unit configured to distribute the magnetic resonance data into the portions. The control device can comprise a reconstruction unit that may execute, for instance, the slice separation algorithm, the undersampling algorithm, and the determination of the actual magnetic resonance image data set. The reconstruction unit may also be configured for recombination of the separately slice-separated portions of the magnetic resonance data.

A computer program product according to the embodiments described herein may be loadable, for example, directly into a memory store of a control device of a magnetic resonance device and may include processor executed code or a suitable program configured to carry out the steps of the method when the computer program is executed in the control device of the magnetic resonance device. The computer program can be stored on an electronically readable data carrier (e.g., a non-transitory computer-readable medium) according to the embodiments described herein, which has electronically readable control information stored thereon, which comprises at least one computer program and is configured such that, on use of the data carrier in a control device of a magnetic resonance device, the control device of the magnetic resonance device carries out the method. Examples of the data carrier include a non-transitory data carrier such as a CD-ROM or any other suitable storage medium.

FIG. 1 illustrates a first flow according to an exemplary embodiment. As shown in FIG. 1, in a first step, reference data 1 for all the slices to be recorded later (in this case a complete sampling of k-space to be sampled), is recorded. For this purpose, a gradient echo sequence, for example, can be used. The complete reference data 1 (i.e., on complete sampling), is used to determine first slice separation kernels 2 of a slice separation algorithm, which in this example is a slice GRAPPA algorithm. In parallel with this, however, by omitting individual k-space lines of the reference data 1, an artificially undersampled reference data set 3 is generated. This is shown in the present case for a degree of scanning in which the slice level describes a factor 2 of the undersampling, so that each second k-space line is shown dashed, i.e., is not sampled. From the artificially undersampled reference data 3, two slice-separation kernels 4 for the slice GRAPPA algorithm are determined so that ultimately slice-separation kernel 2 (complete sampling) and slice-separation kernel 4 (e.g., undersampling by the factor 2) for the different degrees of sampling exist.

Further in accordance with such embodiments, in the later recording of magnetic resonance data, a plurality of slices 5 is scanned simultaneously in the imaging scan with a simultaneous multislice imaging technique, so that "collapsed" magnetic resonance data 6 comes about for the plurality of slices 5 together. Apart from the SMS imaging technique, embodiments include the magnetic resonance data 6 being completely sampled within the slice plane in a first subregion 7, whereas in a second subregion 8 the magnetic resonance data 6 is undersampled with the degree of sampling of the reference data 3, as indicated again by the dashed k-space lines representing omitted k-space lines. As can be seen from FIG. 1, the first subregion 7 extends around k-space center. It should be noted that FIG. 1 (as well as the other Figures) is/are for illustrative purposes and ease of understanding and are not necessarily scaled or otherwise limiting. Embodiments include the first subregion 7 being any suitable size and may be significantly smaller than the sizes as shown in FIG. 1 (and the further Figures) are selected merely for clear recognizability.

In accordance with the present embodiments, in a subsequent step, the magnetic resonance data 6 is divided into a first portion 9 and a second portion 10. The first portion 9 corresponds to the magnetic resonance data 6 of the completely sampled first subregion 7, whilst the second portion 10 corresponds to the magnetic resonance data 6 of the second subregion 8 supplemented with magnetic resonance data 6 of the first subregion 7 such that the sampling pattern as shown is continued. The first portion 9 therefore has a degree of sampling corresponding to a complete sampling, whilst the second portion 10 has a degree of sampling corresponding to the undersampling of the second subregion 8.

In accordance with the present embodiments, in a subsequent step, any suitable slice separation algorithm is applied separately to both portions 9, 10, whereby for the first portion 9, the first slice separation kernels 2 are used and for the second portion 10, the second slice separation kernels 4 are used, as indicated by the arrows 11.

As the result, embodiments include generating slice-separated portions 12, 13, whereby the slice-separated portion 12 is used for calibrating any suitable type of undersampling algorithm (e.g., an in-plane GRAPPA algorithm). Continuing this example, the in-plane GRAPPA algorithm is applied at least to the slice-separated magnetic resonance data 6 of the slice-separated portion 13 belonging to the second subregion 8 to supplement missing magnetic resonance data. Then, the portions 12 and 13 are recombined to slice-separated, supplemented magnetic resonance data 14 completely covering the entire sampled k-space. As a result, for the first subregion 7, either the slice-separated first portion 12 can be used directly, or an averaging with the supplemented slice-separated magnetic resonance data of the slice-separated second portion 13 in the second subregion 7, can take place.

Once the slice-separated, supplemented magnetic resonance data 14 is generated, embodiments include reconstructing a magnetic resonance image data set 15 using nay suitable techniques. These reconstructing techniques may include, for instance, suitable known techniques, and thus the reconstruction techniques are not further discussed herein in greater detail.

FIG. 2 illustrates a second flow according to an exemplary embodiment. The embodiment described with reference to FIG. 2 includes some modifications with respect to the embodiment described with reference to FIG. 1, as further discussed below. For instance, instead of the completely sampled reference data 1 described above with reference to FIG. 1, the exemplary embodiment described with reference to FIG. 2 implements reference data 1', which can be recorded with the degree of sampling of the second subregion 8 (as discussed with reference to FIG. 1 above) and the slice separation kernels 4 may be calculated for this degree of sampling. With further reference to FIG. 2, embodiments include enabling this functionality in that the magnetic resonance data 6 in a first portion 9' and a second portion 10 are subdivided such that the portions 9', 10, each have the degree of sampling of the undersampling in the second subregion 8. For this purpose, the second portion 10 is formed as described for FIG. 1; however, the first portion 9' now only comprises the remaining k-space lines of the first subregion 7 that are not added in the second portion 10. It should be noted here that this may be applicable for the undersampling factor 2 as described herein. At higher undersampling factors in the slice plane, a plurality of first portions 9' is created such that, for all the generated portions 9', 10, the same degree of sampling exists that corresponds to the degree of sampling of the reference data 1' for which the slice separation kernels 4 have been determined. This means that the slice separation kernels 4 can be put to use in accordance with the arrows 11 for all the portions 9', 10.

As shown in FIG. 2, embodiments include the generated slice-separated portions 12', 13 being grouped together into slice-separated preliminary magnetic resonance data 16. Continuing this example, the slice-separated preliminary magnetic resonance data 16 of the first subregion 7 can be used for each of the slices 5 for calibrating the undersampling algorithm that is implemented. Following its use, as shown by the arrow 17, the slice-separated magnetic resonance data 14 is once again available, from which the magnetic resonance image data set 15 may be reconstructed (e.g., in accordance with any suitable known techniques).

FIG. 3 illustrates a third flow according to an exemplary embodiment. The embodiment described with reference to FIG. 3 includes some modifications with respect to the embodiments described with reference to FIGS. 1 and 2, as further discussed below. For instance, the reference data 1 is again recorded completely sampled (similar to the flow describe above with respect to FIG. 1). However, as shown in FIG. 3, one set of slice-separation kernels 4 is calculated for artificially undersampled reference data 3. Further in accordance with the embodiment as shown in FIG. 3, the reference data 1 for the individual slices 5 is additionally used for determining undersampling kernels 18 for the individual slices 5, which are then used according to the arrows 19 to generate, from the slice-separated preliminary magnetic resonance data 16, the slice-separated magnetic resonance data 14 for reconstruction of the magnetic resonance image data set 15.

The exemplary embodiment described with reference to FIG. 3 may be particularly advantageous, for example, when the completely sampled first subregion 7 is too small for a reliable calibration of the undersampling algorithm (e.g., an in-plane GRAPPA algorithm). Moreover, in both the embodiments described with reference to FIGS. 1 and 3, respectively, both reference data 1 and slice-separated scan results of the first subregion 7 can advantageously be used for calibrating the undersampling algorithm, which increases the stability and movement robustness for calibration of the undersampling algorithm (e.g., the in-plane GRAPPA calibration when an in-plane GRAPPA algorithm is implemented).

FIG. 4 illustrates a representation of a magnetic resonance device according to an exemplary embodiment. As shown in FIG. 4, a magnetic resonance device 20 is shown which, as is known in principle, has a main magnet unit 21 (e.g., a suitable magnetic resonance assembly such as a magnetic resonance data acquisition scanner) in which a patient receiving space 22 is defined and into which a patient can be moved by means of a patient support (not shown in detail for purposes of brevity). Furthermore, the magnetic resonance device 20 may include a high frequency coil arrangement and a gradient coil arrangement surrounding the patient receiving space 22.

In an embodiment, the operation of the magnetic resonance device 20 and/or individual components of the magnetic resonance device 20 (e.g., the magnetic resonance data acquisition scanner or other suitable implementation of the main magnet unit 21) is controlled by a control device 23, which is configured to perform the methods (e.g., flows) as described herein. For instance, the operation of the magnetic resonance device 20 and/or individual components of the magnetic resonance device 20 may be controlled by the control device 23 to execute the flows as described herein with reference to FIGS. 1-3. For this purpose, the control device 23 can comprise, for example, a sequence unit (e.g., to perform magnetic resonance sequencing) and a reconstruction unit (e.g., to perform the recombination of the magnetic resonance image data set), as well as a distribution unit for distributing the magnetic resonance data 6 into the portions 9 (or 9', as the case may be) and 10.

In various embodiments, the control device 23 may include one or more suitable processors (e.g., hardware processors, an Application-Specific IC (ASIC), etc.) that may work independently and/or in conjunction with one another to facilitate such functions. For instance, the control device 23 may include and/or access a storage device (e.g., non-transitory computer-readable media such as a ROM, hard disk, non-volatile or volatile memory, etc.) storing executable computer-readable instructions that enable the various components of the magnetic resonance device 20 (e.g., the sequence unit, the reconstruction unit, the distribution unit, etc.) to perform the various embodiments as discussed herein.

Again, the various embodiments described herein may be performed in accordance with the operation of the magnetic resonance device 20, as discussed above. This may include, for example, the various components of the magnetic resonance device 20 working in conjunction with one another and/or other suitable computing components not shown in FIG. 4 for purposes of brevity. For example, the control device 23 may include one or processors that execute algorithms to facilitate operation of the sequence unit, he reconstruction unit, and/or the distribution unit. To provide another example, the control device 23 may be communicatively coupled to other processor(s), storage device(s), network(s), cloud computing device(s), etc., such that any, some, or all of the functions associated with the control device 23 as discussed herein may alternatively or additionally be performed by the device to which the control device 23 is coupled in this manner.

Still further, any portions of the embodiments described herein may be executed manually, semi-autonomously, or fully autonomously. To provide an illustrative example of the overall operation of the embodiments as described herein, one or more components of the magnetic resonance device 20 may generate one or more control signals (or receive one or more control signals from other portions of the magnetic resonance device 20) that result in the execution of various operations. These operations may include, for instance, executing the various algorithms as disused herein (e.g., the multislice imaging algorithm, the slice separation algorithm, the undersampling algorithm, etc.). These operations may further include, for instance, the recording and/or sequencing of magnetic resonance data, simultaneously scanning the plurality of slices 5 in the imaging scan, generating the "collapsed" magnetic resonance data 6, calibrating the slice separation algorithm using reference data, separately executing portions of the magnetic resonance data, recombining the portions of the magnetic resonance data to generate the magnetic resonance image data set, etc.

Moreover, the various data discussed herein that is used in accordance with magnetic resonance image data set acquisition may, once acquired, be stored in any suitable format and in any suitable type of storage medium. For instance, the data may be stored as one or more data files in a memory location that is accessible by the magnetic resonance device 20 and/or the control device 23 as described herein.

In various embodiments, one or more processors associated with the magnetic resonance device 20 and/or the control device 23 may likewise generate one or more control signals in response to user input, in response to the execution of computer-readable instructions, and/or upon accessing or reading the acquired and stored data, such as the various types of data described herein (e.g., recorded data, calibration data, slice data, etc.). The control signals generated via the one or more processors in this manner may thus result in the magnetic resonance device 20 and/or the control device 23 performing the various techniques as described herein. The various computing acts performed by the magnetic resonance device 20 and/or the control device 23 may be in response to any combination of user input and/or control signals that are automatically generated in response to the occurrence of certain events, e.g., upon completion of the multislice imaging algorithm, the slice separation algorithm, undersampling algorithm, etc.

Again, the embodiments of the methods and apparatuses described herein are by way of example and not limitation. The various embodiments described herein may be further modified by a person skilled in the art without departing from the spirit and scope of the disclosure. Furthermore, although the present disclosure has been illustrated and described in detail with the preferred exemplary embodiments, the disclosure is not restricted by the examples given, and other variations can be derived therefrom by a person skilled in the art without departing from the protective scope of the disclosure. Although modifications and changes may be suggested by those skilled in the art, it is the intention of the inventors to embody within the patent warranted hereon all changes and modifications as reasonably and properly come within the scope of their contribution to the art.

It is also pointed out for the sake of completeness that the use of the indefinite articles "a" or "an" does not exclude the possibility that the features in question may also be present more than once. Similarly, the term "unit" does not rule out the possibility that the same consists of a plurality of components which, where necessary, may also be distributed in space.

The claims described herein and the following description in each case contain additional advantages and developments of the embodiments as described herein. In various embodiments, the claims of one claims category can, at the same time, be developed analogously to the claims of a different claims category and the parts of the description pertaining thereto. Furthermore, the various features of different exemplary embodiments and claims may also be combined to create new exemplary embodiments without departing from the spirit and scope of the disclosure.

What is claimed is:

1. A computer-implemented method for recording, using a magnetic resonance device, a magnetic resonance image data set of a region of a patient, the method comprising:
   operating a magnetic resonance data acquisition scanner to execute a multislice imaging algorithm using simultaneous at least partial undersampling in a slice plane to read out magnetic resonance data simultaneously from a plurality of excited slices, the magnetic resonance data being separated into at least two portions, each respective one of the at least two portions being associated with a respective subregion of sampled k-space in the slice plane of the magnetic resonance data having a different fixed degree of sampling;
   calibrating, via the magnetic resonance data acquisition scanner, a slice separation algorithm using reference data that is recorded in a separate reference scan;
   separately executing, via the magnetic resonance data acquisition scanner, for each respective one of the at least two portions of the magnetic resonance data associated with a respective subregion of the sampled k-space, the calibrated slice separation algorithm to the simultaneously read out plurality of excited slices to generate respective slice-separated portions, the calibrated slice separation algorithm utilizing a different respective slice separation kernel for each respective one of the at least two portions of the magnetic resonance data;
   executing, via the magnetic resonance data acquisition scanner, an undersampling algorithm to undersampled magnetic resonance data associated with the slice-separated portions having a fixed degree of sampling associated with undersampling to compensate for the at least partial undersampling in the slice plane; and
   recombining slice-by-slice, via the magnetic resonance data acquisition scanner after compensation of the undersampling in the slice plane, the respective slice-separated portions of the magnetic resonance data to generate the magnetic resonance image data set.

2. The method as claimed in claim 1, wherein the reference data is recorded with a complete sampling of k-space and by omitting part of the reference data to determine at least one slice separation kernel for the slice separation algorithm such that an artificial undersampling of the reference data corresponds to the undersampling of the respective one of the at least two portions of the magnetic resonance data for which the slice separation kernel is to be used.

3. The method as claimed in claim 2, wherein each respective one of the at least two portions of the magnetic resonance data corresponds to a different degree of sampling, and
   wherein at least one corresponding slice separation kernel is determined for each respective one of the at least two portions of the magnetic resonance data.

4. The method as claimed in claim 1, wherein each respective one of the at least two portions of the magnetic resonance data has the same degree of sampling.

5. The method as claimed in claim 4, wherein the reference data is recorded with the same degree of sampling as each respective one of the at least two portions of the magnetic resonance data.

6. The method as claimed in claim 4, wherein the at least two portions of the magnetic resonance data include a first portion associated with a first subregion of sampled k-space in the slice plane of the magnetic resonance data and a second portion associated with a second subregion of sampled k-space in the slice plane of the magnetic resonance data,
   wherein upon complete sampling of the first subregion about k-space center and undersampling of the second subregion comprising remaining k-space, k-space lines are added from the first subregion to the second portion by continuing the sampling pattern of the second subregion, and
   wherein the remaining magnetic resonance data of the first subregion having undersampling that corresponds to that of the second portion is further processed.

7. The method as claimed in claim 1, wherein one of the at least two portions of the magnetic resonance data corresponding to a subregion of sampled k-space in the slice plane of the magnetic resonance data having a higher degree of sampling is used for calibrating the undersampling algorithm.

8. The method as claimed in claim 1, wherein at least one completely sampled portion of the reference data is used for calibrating the undersampling algorithm.

9. The method as claimed in claim 1, wherein the slice separation algorithm includes a slice Generalized Autocalibrating Partially Parallel Acquisitions (GRAPPA) algorithm.

10. The method as claimed in claim 1, wherein the undersampling algorithm includes an in-plane Generalized Autocalibrating Partially Parallel Acquisitions (GRAPPA) algorithm.

11. The method as claimed in claim 1, wherein the magnetic resonance data is generated using a blipped Controlled Aliasing in Parallel Imaging (CAIPI) technique as the multislice imaging technique.

12. The method as claimed in claim 1, wherein the magnetic resonance data is generated using a magnetic resonance sequence that includes a turbospin echo (TSE) sequence.

13. A magnetic resonance device for recording a magnetic resonance image data set of a region of a patient, comprising:
a magnetic resonance data acquisition scanner;
a patient receiving space configured to receive the patient; and
a control device configured to operate the magnetic resonance data acquisition scanner to:
execute a multislice imaging algorithm using simultaneous at least partial undersampling in a slice plane to read out magnetic resonance data simultaneously from a plurality of excited slices, the magnetic resonance data being-separated into at least two portions, each respective one of the at least two portions being associated with a respective subregion of sampled k-space in the slice plane of the magnetic resonance data having a different fixed degree of sampling;
calibrate a slice separation algorithm using reference data that is recorded in a separate reference scan;
separately execute, for each respective one of the at least two portions of the magnetic resonance data associated with a respective subregion of the sampled k-space, the calibrated slice separation algorithm to the simultaneously read out plurality of excited slices to generate respective slice-separated portions, the calibrated slice separation algorithm utilizing a different slice separation kernel for each respective one of the at least two portions of the magnetic resonance data;
execute an undersampling algorithm to undersampled magnetic resonance data associated with the slice-separated portions having a fixed degree of sampling associated with undersampling to compensate for the at least partial undersampling in the slice plane; and
recombine, slice-by-slice after compensation of the undersampling in the slice plane, the respective slice-separated portions of the magnetic resonance data to generate the magnetic resonance image data set.

14. The magnetic resonance device as claimed in claim 13, wherein the control device is configured to operate the magnetic resonance data acquisition scanner to record the reference data with a complete sampling of k-space and by omitting part of the reference data to determine at least one slice separation kernel for the slice separation algorithm such that an artificial undersampling of the reference data corresponds to the undersampling of the respective one of the at least two portions of the magnetic resonance data for which the slice separation kernel is to be used.

15. The magnetic resonance device as claimed in claim 14, wherein each respective one of the at least two portions of the magnetic resonance data corresponds to a different degree of sampling, and
wherein the control device is configured to operate the magnetic resonance data acquisition scanner to determine at least one corresponding slice separation kernel for each respective one of the at least two portions of the magnetic resonance data.

16. The magnetic resonance device as claimed in claim 13, wherein:

each respective one of the at least two portions of the magnetic resonance data has the same degree of sampling,
the at least two portions of the magnetic resonance data include a first portion associated with a first subregion of sampled k-space in the slice plane of the magnetic resonance data and a second portion associated with a second subregion of sampled k-space in the slice plane of the magnetic resonance data,
the control device is configured to, upon complete sampling of the first subregion about k-space center and undersampling of the second subregion comprising remaining k-space, operate the magnetic resonance data acquisition scanner to add k-space lines from the first subregion to the second portion by continuing the sampling pattern of the second subregion, and to further process the remaining magnetic resonance data of the first subregion having undersampling that corresponds to that of the second portion.

17. A non-transitory computer readable medium loaded onto a control device of a magnetic resonance data acquisition scanner for recording a magnetic resonance image data set of a region of a patient, the non-transitory computer readable medium having instructions stored thereon that, when executed by the control device, cause the magnetic resonance data acquisition scanner to:
execute a multislice imaging algorithm using simultaneous at least partial undersampling in a slice plane to read out magnetic resonance data simultaneously from a plurality of excited slices, the magnetic resonance data being separated into at least two portions, each respective one of the at least two portions being associated with a respective subregion of sampled k-space in the slice plane of the magnetic resonance data having a different fixed degree of sampling;
calibrate a slice separation algorithm using reference data that is recorded in a separate reference scan;
separately execute, for each respective one of the at least two portions of the magnetic resonance data associated with a respective subregion of the sampled k-space, the calibrated slice separation algorithm to the simultaneously read out plurality of excited slices to generate respective slice-separated portions the calibrated slice separation algorithm utilizing a different slice separation kernel for each respective one of the at least two portions of the magnetic resonance data;
execute an undersampling algorithm to undersampled magnetic resonance data associated with the slice-separated portions having a fixed degree of sampling associated with undersampling to compensate for the at least partial undersampling in the slice plane; and
recombine, slice-by-slice after compensation of the undersampling in the slice plane, the respective slice-separated portions of the magnetic resonance data to generate the magnetic resonance image data set.

18. The non-transitory computer readable medium as claimed in claim 17, wherein the reference data is recorded with a complete sampling of k-space and by omitting part of the reference data to determine at least one slice separation kernel for the slice separation algorithm such that an artificial undersampling of the reference data corresponds to the undersampling of the respective one of the at least two portions of the magnetic resonance data for which the slice separation kernel is to be used.

19. The non-transitory computer readable medium as claimed in claim 18, wherein each respective one of the at least two portions of the magnetic resonance data corresponds to a different degree of sampling, and wherein the non-transitory computer readable medium further includes instructions that, when executed by the control device, cause the magnetic resonance data acquisition scanner to determine at least one corresponding slice separation kernel for each respective one of the at least two portions of the magnetic resonance data.

20. The non-transitory computer readable medium as claimed in claim 17, wherein:

each respective one of the at least two portions of the magnetic resonance data has the same degree of sampling, the at least two portions of the magnetic resonance data include a first portion associated with a first subregion of sampled k-space in the slice plane of the magnetic resonance data and a second portion associated with a second subregion of sampled k-space in the slice plane of the magnetic resonance data, the non-transitory computer readable medium further includes instructions that, when executed by the control device, cause the magnetic resonance data acquisition scanner to, upon complete sampling of the first subregion about k-space center and undersampling of the second subregion comprising remaining k-space, add k-space lines from the first subregion to the second portion by continuing the sampling pattern of the second subregion, and to further process the remaining magnetic resonance data of the first subregion having undersampling that corresponds to that of the second portion.

* * * * *